United States Patent

Faust et al.

[11] Patent Number: 5,981,785
[45] Date of Patent: Nov. 9, 1999

[54] SILYL-FUNCTIONAL INITIATOR FOR LIVING CATIONIC POLYMERIZATION

[75] Inventors: Rudolf Faust, Lexington; Savvas E. Hadjikyriacou, Lowell, both of Mass.; Toshio Suzuki, Midland, Mich.

[73] Assignees: University of Massachusetts, Lowell, Mass.; Dow Corning Corporation, Midland, Mich.

[21] Appl. No.: 09/204,900

[22] Filed: Dec. 3, 1998

[51] Int. Cl.⁶ .................................................. C07F 7/12
[52] U.S. Cl. .......................................... 556/488; 556/436
[58] Field of Search .................... 526/279; 556/488, 556/436

[56] References Cited

U.S. PATENT DOCUMENTS

| | | | |
|---|---|---|---|
| 3,925,434 | 12/1975 | Chuang | 260/448.2 |
| 4,503,208 | 3/1985 | Lin et al. | |
| 4,504,629 | 3/1985 | Lien et al. | |
| 4,575,545 | 3/1986 | Nakos et al. | |
| 4,675,346 | 6/1987 | Lin et al. | |
| 4,699,802 | 10/1987 | Nakos et al. | |
| 4,760,122 | 7/1988 | Nakos et al. | |
| 4,904,732 | 2/1990 | Iwahara | 525/100 |

OTHER PUBLICATIONS

In–House Abstract pp. 19–21 Answer 11 of 12–1984:510995 DN101:110995–Manuel et al. J. Organomet. Chem (1984) 264 (1–2), 127–133.

Journal of Polymer Science; Polymer Chemistry Edition, vol. 17, 2129–2136 (1979); J. Ambrose and J. Newell, "Cationic Polymerization of alpha–Methylstyrene from olydienes."

Journal of the American Chemical Society, vol. 95, 6386–6390 (1973); Kennedy, et al, "Alkylation of Tertiary Alkyl Halides with Trialkylaluminums."

Advances in Polymer Science, vol. 28, 83–111 (1978); Kennedy, et al, "Cationic Olefin Polymerization Using Alkyl Halide Alkylaluminum Initiator Systems."

Journal of Organometallic Chemistry, 156 (1978) 55–64; Sivaram, "Organoaluminum Chemistry and its Application to the Initiation of Carbenium Ion Polymerization."

Advances in Polymer Science, vol. 43, 3–50 (1982); Kennedy, et al, Carbocationic Synthesis and Characterization of Polyolefins with Si–H and Si–CL Head Groups.

*Primary Examiner*—Bernard Lipman
*Assistant Examiner*—N. Sarofim
*Attorney, Agent, or Firm*—Alex Weitz

[57] ABSTRACT

A novel initiator which may be used to prepare a silyl-functional living cationic polymer is disclosed, said initiator having the formula

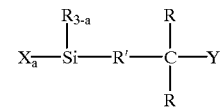

wherein R is independently selected from the group consisting of alkyl groups having 1 to 10 carbon atoms and aryl groups having 6 to 10 carbon atoms, R' is a divalent aliphatic hydrocarbon group having at least 3 carbon atoms, X is halogen, Y is selected from the group consisting of halogen, alkoxy, acyloxy and hydroxyl groups and a is 1, 2 or 3.

5 Claims, No Drawings

SILYL-FUNCTIONAL INITIATOR FOR LIVING CATIONIC POLYMERIZATION

FIELD OF THE INVENTION

The present invention relates to an initiator for preparing a living cationic polymers. More particularly, the invention relates to a novel haloorganosilane initiators which can be reacted with a cationically polymerizable monomer in the presence of a Lewis acid to provide a living polymer having a silyl-functional head group.

BACKGROUND OF THE INVENTION

Living anionic polymers are well known in the art but relatively few truly living cationic systems have been studied. By definition, termination and chain transfer rates are zero or negligible in such a living polymer so that the concentration of active centers remains approximately constant. Of particular commercial interest are living organic polymers which can be used to prepare telechelic oligomers and macromolecules having hydrolyzable silyl end groups since these can be used to formulate room temperature vulcanizable (RTV), moisture-curable sealants, caulks and adhesives, inter alia. Unlike the well known moisture-curable silicone RTVs, compositions based on polymers having a hydrocarbon backbone offer the advantage of low permeability, making them more suitable for gas barrier applications such as form-in-place gaskets, O-rings, rubber plugs/seals, and the like.

Polymers having reactive silyl head groups were described by Kennedy et al. in *Advances in Polymer Science*, 43, 1–50 (1982). These workers discovered that initiators which included an SiCl or SiH group as well a cationogenic moiety could be used to polymerize cationic systems such that the silicon-functional groups survived. The cationogenic moiety studied was the benzyl chloride group (i.e., —$C_6H_4$—$CH_2Cl$) wherein α-methylstyrene was polymerized in the presence of diethyl aluminum chloride as coinitiator. In this case, however, it was observed that the amount of —SiCl detected was only a small fraction of the theoretical, especially when more than one chlorine was present in the head group. Further, although these workers suggest that the SiCl groups may survive polymerization of isobutylene, they did not obtain quantitative confirmation thereof and did not demonstrate the new initiators in connection with this monomer. Thus, Kennedy et al. then turned to the investigation of systems having SiH terminal groups, such polymers being considered more promising intermediates which presented fewer experimental difficulties.

Therefore, there is still a need for a compound which is capable of initiating a cationic polymerizable monomer such as isobutylene to prepare a polymer having a reactive silicon-functional head group.

SUMMARY OF THE INVENTION

Applicants have now discovered a novel class of compounds which can initiate cationic polymerization in the presence of a Lewis acid to provide a polymer having a silicon halide head group. The present invention, therefore, relates to an initiator of the formula

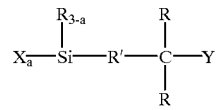

wherein R is independently selected from alkyl groups having 1 to 10 carbon atoms or aryl groups having 6 to 10 carbon atoms, R' is a divalent aliphatic hydrocarbon group having at least 3 carbon atoms, X is halogen, Y is selected from halogen, alkoxy, acyloxy or hydroxyl groups and a is 1, 2 or 3.

DETAILED DESCRIPTION OF THE INVENTION

The reactive silyl-functional initiators of the present invention are represented by the formula

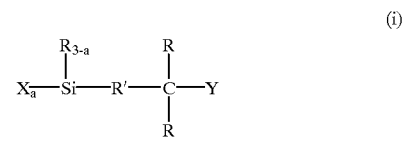

(i)

wherein R is independently selected from alkyl groups having 1 to 10 carbon atoms or aryl groups having 6 to 10 carbon atoms, such as methyl, ethyl, propyl, isopropyl, n-butyl, isobutyl, n-octyl, 2-ethylhexyl, n-nonyl, n-decyl, phenyl, benzyl and tolyl, methyl being preferred.

In formula (i), R' is a divalent aliphatic hydrocarbon group having at least 3 carbon atoms. Non-limiting examples of R' include linear and branched connecting groups such as propylene, butylene, neopentylene and hexylene. Difficulties were encountered in attempts to prepare low molecular weight polymers using initiators of similar structure wherein R' has fewer than 3 carbons. The skilled artisan will appreciate that control of molecular weight is important, low values thereof being particularly desirable in the formulation of sealants, coatings and adhesives. Moreover, it was also found that initiators wherein R' has fewer than the above mentioned 3 carbons are generally difficult to prepare by the traditional hydrosilation routes described infra, a mixture of isomers which are hard to hydrochlorinate being obtained, as described infra.

Other than the above limitation, there is no specific limit on the size of the R' group. However, from a practical perspective, it is preferred that this group have no more than 10 carbons since larger values make it quite difficult to purify the corresponding initiator by standard techniques.

X in formula (i) is halogen, such as fluorine, chlorine, bromine or iodine, preferably chlorine. Y is selected from the group consisting of halogen, alkoxy having 1 to 10 carbon atoms, acyloxy having 2 to 10 carbon atoms and hydroxyl and a is 1, 2 or 3. Preferably, Y is chlorine and a is 2 or 3.

A highly preferred initiator has the formula

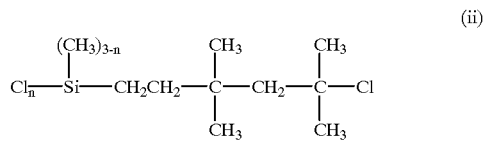

(ii)

in which n is 2 or 3.

The initiators of the present invention can be prepared by hydrosilating a compound of the formula

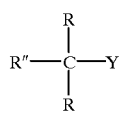
(iii)

in which R" is an ethylenically unsaturated monovalent group corresponding to the group R' of formula (i) (e.g., when R' is —CH$_2$CH$_2$CH$_2$—, R" is CH$_2$=CH—CH$_2$—) with a hdridosilane of the formula

(iv)

the molar ratio of component (iii) to component (iv) generally being 0.3 to 3, preferably 1. When the molar ratio is not 1, or if the reaction does not proceed to completion, removal of the unreacted reactants is recommended. In formulas (iii) and (iv), R, X, Y and a have their previously defined meanings and the reaction is carried out in the presence of a hydrosilation catalyst. Alternatively, the initiator may be prepared by a conventional Grignard synthesis.

Suitable catalysts for the above reaction are platinum black, platinum metal on various solid supports (e.g., carbon), chloroplatinic acid, alcohol solutions of chloroplatinic acid, and complexes of chloroplatinic acid with liquid ethylenically unsaturated compounds such as olefins and organopolysiloxanes containing ethylenically unsaturated hydrocarbon radicals bonded to silicon. Preferred catalysts include a platinum complex catalyst produced by reacting chloroplatinic acid and divinyltetramethyldisiloxane, prepared according to U.S. Pat. No. 3,419,593 to Willing and a neutralized complex of platinous chloride and divinyltetramethyldisiloxane, prepared according to U.S. Pat. No. 5,175,325 to Brown et al., these patents being hereby incorporated by reference. Most preferably, this catalyst is a neutralized complex of platinous chloride and divinyltetramethyldisiloxane. For this synthesis, the hydrosilation catalyst is generally employed at a level equivalent to a platinum concentration of from 0.1 to 1,000 parts by weight of platinum metal, preferably from to 1 to 100 parts by weight of platinum metal, per million weight parts (ppm) of the unsaturated component (ii).

During the preparation of the initiator, it has been observed that spontaneous dehydrochlorination can take place (i.e., when X=Cl). In this event, the hydrosilated product can be reacted with hydrochloric acid by bubbling dry HCl into a solution thereof for 3 to 5 hours at 0° C. to provide the desired initiator in quantitative yield. Further, such a dehydrochlorination can be kept to a minimum by conducting the hydrosilation below room temperature.

The above described initiators can be used to cationically polymerize vinyl monomers which can stabilize a cation or propagating center due to the presence of an electron donating group, or by resonance. This polymerization is carried out in the presence of a Lewis acid and the monomers may be selected from alkenes, such as isobutylene, butadiene, isoprene, methylbutene, 2-methylpentene; styrenics, such as styrene, p-methylstyrene, α-methylstyrene and indene, inter alia. Alternatively, the monomers can be vinyl ethers, such as isobutyl vinyl ether and methyl vinyl ether. Use of mixtures of one or more of the above described monomers is also contemplated.

It is preferred that at least one monomer is selected from isobutylene, isoprene or a styrenic monomer. Preferably, at least 50 mole percent, and more preferably 80 mole percent, of the monomer used in the cationic polymerization is isobutylene. Most preferably, the entire monomer is isobutylene, this resulting in a living polyisobutylene (PIB) homopolymer when polymerized as described infra.

The Lewis acid, employed as a co-initiator, is of the type known to catalyze at least one cationic living polymerization. Examples of such Lewis acids include BZ$_3$, TiZ$_4$, AlZ$_3$, SnZ$_4$ and ZnZ$_2$, inter alia, wherein Z is independently selected from the group consisting of halogen, alkoxy having 1 to 4 carbon atoms and alkyl having 1 to 4 carbon atoms. Preferably Z is halogen, most preferably chlorine. Of course, those skilled in the art will recognize that a compound such as TiZ$_4$ in which all of the Z groups are alkyl groups is not a useful catalyst for cationic living polymerization and such compounds are not contemplated herein. The interested reader is referred to the article by Matyjaszewski and Pugh in *Cationic Polymerization Mechanism, Synthesis and Applications*, Matyjaszewski, Ed.; Marcel Dekker, New York (1996), for a review of suitable Lewis acids. Preferably, the Lewis acid is selected from TiCl$_4$ or a mixture of BCl$_3$ and BBr$_3$.

In order to prepare a living cationic polymer using the initiators of the invention, at least one monomer (A) is polymerized with an initiator of the formula (i) in the presence of a Lewis acid. Additionally, a Lewis base, such as pyridine or its derivatives, such as 2,6-ditert-butyl-pyridine (DTBP) or lutidine, is preferably included in this polymerization reaction in order to prevent initiation by protic impurities. Such cationic living polymerizations are well known in the art, including typical reaction conditions and proportions of the monomer(s), initiator, Lewis acid, etc. This polymerization can be carried out in the vapor phase but is preferably run in a dry organic solvent solution (e.g., hexane, methylene chloride, methyl chloride, toluene, and combinations thereof). Of course, these conditions will vary according to the particular ingredients under consideration and optimization of conditions and proportions needed to obtain a particular living polymer having a desired molecular weight can be achieved through routine experimentation by those skilled in the art. For example, the interested reader is directed to the chapter by Sawamoto in *Cationic Polymerization Mechanism, Synthesis and Applications*, Matyjaszewski, Ed.; Marcel Dekker, New York (1996) and the text by Kennedy and Ivan entitled *Designed Polymers by Carbocationic Macromolecular Engineering: Theory and Practice* published by Hanser (1992).

In a preferred embodiment, isobutylene (IB) is reacted with an initiator according to formula (ii) in the presence of TiCl$_4$. This reaction is carried out in a solvent, preferably a combination of methyl chloride and hexanes in a volume ratio of about 60/40 to 40/60, as well as in the presence of a Lewis base, such as DTBP, under dry conditions and at a temperature of −100 to 0° C., preferably −80° C. to −60° C. Preferably, the order of addition is solvent, Lewis base, Lewis acid, initiator and monomer. The concentrations of the initiator and TiCl$_4$ are preferably about 10$^{-3}$ to 10$^{-1}$ molar (M) and 10$^{-3}$ to 10$^{-2}$M, respectively, based on the total solution, while the molar content of DTBP is adjusted to be equal or greater than that of protic impurity.

When the above described polymerization procedure is deemed complete, preferably when monomer conversion is at least 98%, the resulting living polymer may quenched with, e.g., pyridine, to provide a stable polymer having

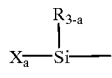

head groups, wherein R, X and a have their previously defined meanings. Alternatively, the living polymer may be quenched with an alcohol, preferably having 1 to 4 carbon atoms, to form a similar stable polymer wherein the X groups are replaced with the corresponding alkoxy group. For example, when methanol is the quenching agent, the SiX functionality undergoes methanolysis and the resulting polymer has a head group of the structure

wherein R and a have their previously defined meanings and Me hereinafter denotes methyl.

The initiators of the invention may also be used to prepare telechelic polymers of the type A—A and AB-BA, inter alia, wherein A and B represent different polymer blocks. These structures are obtained by coupling two of the above described cationic living polymers of the type A$^+$ or AB$^+$, respectively. Such a coupling preferably doubles the molecular weight of the living polymer to provide a silyl-functional telechelic polymer. This may be accomplished by reacting the living polymer with a compound known in the art to couple such cationic systems.

For example, non-ionic coupling agents, such as bifunctional silyl enol ethers can be employed in the coupling of short living chains of poly(isobutyl vinyl ether). In-situ coupling of living polyisobutylene (PIB) can be carried out using a bis-diphenylethylenes (bis-DPE) such as 2,2-bis{4-(1-phenylethenyl)phenyl}propane and 2,2-bis{4-(1-tolylethenyl)phenyl}propane where the two DPE moieties are separated by a spacer bar (Bae et al. in *Macromolecules*, 30, 198, (1997)). Also, coupling of oligomeric polyisobutylene can be accomplished through ω-isopropenyl functionality (—CH$_2$C(CH$_3$)═CH$_2$) using catalytic amounts of triflic acid (CF$_3$SO$_3$H) in hexanes at −80° C. (Coca et al. in *Macromolecules*, 30, 649 (1997)).

Preferably, the coupling agent is an organic compound having at least 2 furan rings in its molecule and the coupling reaction takes place in the presence of a Lewis acid of the type described supra. An example of this agent is

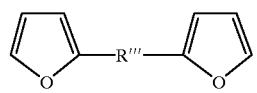

(v)

wherein R'" is a straight chain or branched alkylene group having 1 to 10 carbon atoms, preferably at least 2 carbon atoms, which may also contain cyclic structures such as aromatic rings, furan rings, and the like, in either pendant positions or in the alkylene chain. Preferably, the furan coupling agent has the structure

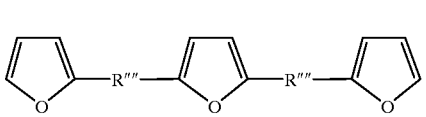

(vi)

wherein R"" is independently selected from alkylene groups having 1 to 10 carbon atoms. Specific preferred coupling agents are represented by the following structures:

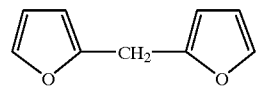

difuranylmethane (DFM),

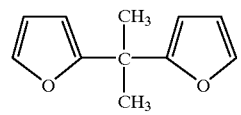

2, 2-difuranylpropane (DFP),

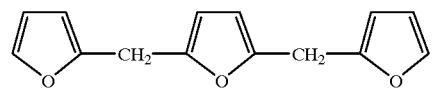

2, 5(bis-2-furanylmethylene)furan (bFMF)

and

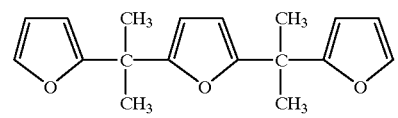

bis(2-furanyl-isopropyl)-furan (bFPF)

bFMF and bFPF being preferred.

The coupling reaction using the furan compounds is typically carried out in an organic solvent solution such as would ordinarily be used to conduct the actual cationic polymerization. Optimum reaction conditions for a given set of components can be determined by those skilled in the art through routine experimentation, but coupling is typically accomplished at a temperature of about −80° C. to about 40° C. It will be recognized, however, that this temperature will greatly depend upon the particular living polymer under consideration. For example, in the case of the preferred polyisobutylene living cationic polymers, this temperature is preferably −80° C. to −60° C. A stoichiometric amount of the furan coupling agent relative to the concentration of living chain ends is preferred, however, a slight excess of the coupling agent over this stoichiometric equivalent amount of coupling agent for each mole of chain end can be used. It is further contemplated that the coupling reaction can be accomplished in the same vessel used for the polymerization and the solvents, as well as Lewis acid used in the former reaction, can be retained during the coupling reaction (i.e., a one-pot procedure).

In a preferred embodiment wherein the Lewis acid is TiCl$_4$ and the living polymer is PIB, the Lewis acid is typically added at a level of at least two times the living polymer concentration. In general, optimum Lewis acid levels employed will depend on such factors as Lewis acid type, monomer type and solvent type, inter alia. Typically, the Lewis acid content is already in the above recited range (i.e., from the preparation of the living polymer) and further addition thereof is not necessary.

There is no critical order of addition of the components for the coupling. In a typical procedure, the furan compound and Lewis acid (if a sufficient amount is not provided during the polymerization step) are added to a solution of the living polymer.

When the highly preferred agent bFPF is employed to couple living polyisobutylene, the coupling efficiency is generally quite high and the number average molecular weight of the PIB is essentially doubled, within experimental error (i.e., quantitative coupling). Even when a less preferred furan compound such as DMF or DFP is used, some increase of molecular weight (e.g., 30–50%) is observed. However, when a compound having only one furan ring such as furan itself is used, the coupling reaction does not proceed and molecular weight remains essentially constant.

After completion of the coupling reaction, as indicated by molecular weight increase or depletion of coupling agent, the resulting polymer may be isolated by conventional techniques, such as precipitation from solution by the addition of a poor solvent for the polymer.

When the preferred silyl-functional PIB living polymer is coupled with the above described furan compounds (v) or (vi), one obtains telechelic PIB polymers having the respective formulas

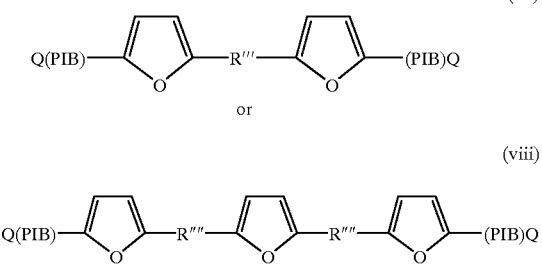

wherein R''' and R'''' are defined above, PIB represents the polyisobutylene chain residue and Q is a moiety which contains the functional silyl group introduced by the initiator having the formula

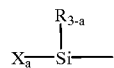

wherein R, X and a have their previously defined meanings. As described above, these halogen-functional silyl groups can be converted to the corresponding alkoxy-functional silyl groups by reaction with an alcohol to provide the above telechelic polymers wherein the end groups have the formula

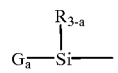

in which R and a are as defined above and G is an alkoxy group, preferably having 1 to 4 carbon atoms, most preferably methoxy.

The initiators of the present invention may be used to prepare silyl-functional cationic living polymers which find utility as a filler treatment or in the modification of solid surfaces (e.g., as a hydrophobing agent).

When the above living systems are coupled to provide telechelic polymers, the latter can be cured by exposure to moisture and can therefore be employed as base polymers in the formulation of sealants, adhesive and coatings when combined with the appropriate catalysts, inter alia. Those skilled in the art will, of course, appreciate that at least one crosslinker would be necessary to obtain a cured system when there is only one reactive group on silicon (i.e., when a=1 in the above formulae). When cured, these formulated compositions can be used as form-in-place gaskets, seals for insulating glass, and the like.

EXAMPLES

The following examples are presented to further illustrate the initiator of this invention, but are not to be construed as limiting the invention, which is delineated in the appended claims. All parts and percentages in the examples are on a weight basis and all measurements were obtained at 25° C. unless indicated to the contrary.

Example 1

Preparation of 1-methyldichlorosilyl-3,3,5-trimethyl-5-chloro-hexane.

Into a dry 25 ml two neck round bottom flask equipped with a magnetic stirrer and a drying tube filled with DrieriteTM were placed 1.0 g of 3,3,5-trimethyl-5-chloro-1-hexene (TMHCl), (6.23 mmoles). Using a syringe, 1.0 ml (9.6 mmol) of $CH_3Cl_2SiH$ was injected. The mixture was stirred for 5 minutes and then 50 µl of a 10% solution of platinum-divinyltetramethyldisiloxane complex in hexanes was injected and the system was allowed to react at room temperature.

The progress of the reaction was monitored by $^1H$ NMR spectroscopy. A small sample was withdrawn at various times and was injected into dried $CDCl_3$ in an NMR tube. The tube was sealed under $N_2$ and the spectrum was recorded immediately. The reaction was continued until the $^1H$ NMR spectrum showed completion (i.e., disappearance of the double bonds). After 30 hours of reaction, a condenser was installed to prevent any further losses by evaporation. $^1H$ NMR spectrum indicated that the concentration of $CH_3Cl_2SiH$ had become low, while substantial amounts of double bond containing groups were still present. For this reason an additional 1 ml of $CH_3Cl_2SiH$ was injected to keep its concentration in excess over TMHCl. The reaction was complete within 48 hours.

As indicated by $^1H$ NMR spectroscopy, the presence of double bonds at 4.6 and 4.8 ppm indicated that HCl elimination (16.6%) from the chloro end of the product had occurred. The product was therefore re-hydrochlorinated by dissolving it in dried $CH_2Cl_2$ and bubbling dried HCl therethrough for 3 hours at 0° C. The excess HCl and solvents were evaporated on a Rotavap™ to give 1.2425 g of 1-methyldichlorosilyl-3,3,5-trimethyl-5-clorohexane as confirmed by $^1H$ NMR (73% yield):

(INITIATOR 1)

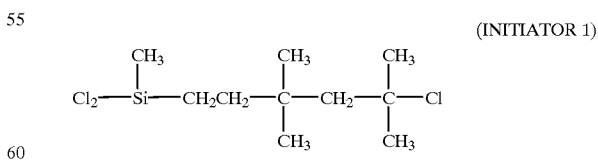

Example 2

Synthesis of the Coupling Agents 2,2-difuryl-propane (DFP) and 2,5-bis-(2-furyl-propyl)-furan (bFPF).

Furan (50 ml, 46.8 g) and acetone (25 ml, 19.7 g) were placed into a three neck 250 ml flask equipped with a condenser, an addition funnel and a magnetic stirring bar. The mixture was cooled to 0° C. by means of an ice-bath. While stirring, 10 ml of concentrated HCl (37%) were added dropwise. After the HCl addition, the ice bath was removed allowing the temperature of the reaction mixture to rise to room temperature and the system was stirred for an additional 3 hours. The mixture was then diluted with an equal volume of hexanes and washed until neutral with 10% aqueous sodium carbonate ($Na_2CO_3$) solution followed by distilled water. The mixture was left overnight over drying agent ($Na_2SO_4$).

The next day 24 g of 2,2-difuryl-propane (DFP) and 6 g of 2,5-bis-(2-furyl-propyl)-furane (bFPF) were recovered by distillation under vacuum. The bFPF was further purified by recystallization from methanol to give white needles having a melt point of 47° C.–48° C. $^1$HNMR analysis confirmed the target compounds.

Example 3

Polymerization of Isobutylene (IB) Followed by In-situ Coupling of the Living Polymer Into a 250 ml two neck round bottom flask cooled to −80° C. were placed 47.5 ml of hexanes (measured at room temperature). After being cooled down to the reaction temperature, 31 ml (measured at −80° C.) of $CH_3Cl$ were stirred in. A solution of 0.08 ml of 2,6-ditert-butyl-pyridine (DTBP) in 10 ml of hexanes which had been cooled to −80° C. was added next, followed by a solution of 1.1 ml of $TiCl_4$ in a mixture of 10 ml hexanes and 10 ml $CH_3Cl$. The mixture was stirred for five minutes and 0.6913 g of INITIATOR 1 (prepared in Example 1) was introduced as a solution in a mixture of 10 ml hexanes/5 ml $CH_3Cl$ that was also kept at −80° C. This was immediately followed by the addition of 10 ml of IB, the latter then being polymerized over a period of 40 minutes to form a living system. A 25 ml sample of the resulting cationic living polymer was removed and quenched with anhydrous methanol to provide a control polymer. Upon quenching, the chloro-groups on silicon underwent methanolysis, as evidenced by a methoxy peak at 3.5 ppm in the $^1$H NMR spectrum. This control was purified by precipitation from hexanes/methanol under $N_2$ and traces of solvents were removed under

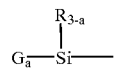

vacuum (overnight). Characterization by gel permeation chromatography (GPC) showed a number average molecular weight ($M_n$) of 3,200 (theoretical $M_n$=2,800).

A solution of 0.2357 g of 2,5-bis-(2-furyl-propyl)-furane (bFPF) in 6 ml of $CH_3Cl$ was added to the remaining living polymer solution (essentially at 100% conversion). The reaction was also quenched with excess anhydrous methanol after 90 minutes to neutralize the Lewis acid.

Final molar concentrations of the reactants (based on the total solution) were as follows:

INITIATOR 1=$2 \times 10^{-2}$M; DTBP=$3 \times 10^{-3}$M; $TiCl_4$=$8 \times 10^{-2}$M; IB=1.0M; bFPF=$8.3 \times 10^{-3}$M.

The coupled polyisobutylene (PIB) polymer was purified and devolatilized, as described above. Its $M_n$ had increased to 5,300. Further, $^1$H NMR spectroscopy indicated that the coupling efficiency was 84% (i.e., essentially a methoxysilyl-functional telechelic polymer containing 16% monoaddition product).

Example 4

Crosslinking of the Coupled Polymer

The telechelic PIB prepared in Example 3 (1.0764 g) was mixed with 0.0512 g of tin octoate (tin-2-ethylhexanoate) and 1 drop of water in a 50 ml beaker. The mixture was stirred manually to give a cured white homogeneous elastomeric mass which was then allowed to stand for 72 hours. Hexanes (32 ml) were added and the combination was agitated using a magnetic stirrer for another 72 hours. The resulting swelled polymer was then filtered and the hexanes evaporated under vacuum. The dried cured polymer weighed 1.0415 g, corresponding to 96.8% of the original polymer weight (i.e., 3.2% was the soluble fraction).

(Comparative) Example 5

Preparation of 1-methyldichlorosilyl-3-methyl-3-chlorobutane

Into a 250 ml two neck reaction flask equipped with a magnetic stirrer, a condenser and a drying tube were placed 20 ml of isoprene. While stirring, 1.3 ml of platinum-divinyltetramethyldisiloxane (10% in hexanes) was injected. The system was refluxed gently and then $CH_3Cl_2SiH$ (31.3 ml) was added dropwise. The addition rate was such as to maintain gentle refux. After the addition of $CH_3Cl_2SiH$, refluxing was continued for 4 hours. The reaction mixture was cooled to room temperature and a sample taken for structural verification.

$^1$H NMR analysis indicated that the mixture contained the following two isomers (a) 4-methyldichlorosilyl-2-methyl-2-butene (80 mol %) and (b) 1-methyldichlorosilyl-2-methyl-2-butene (20 mol %), but none of the expected product (c) 4-methyldichlorosilyl-2-methyl-1-butene.

The above isomeric structures were further confirmed by the following analytical techniques: $^{13}$C NMR, Distortionless Enhancement by Polarization Transfer (DEPT 135) and Heteronuclear chemical shift Correlation spectroscopy (HETCOR).

To the mixture of isomers there was added dried, distilled $CH_2Cl_2$ to make up a 30% solution. Dry HCl was bubbled through the solution for 6 hours at 0° C., whereupon a sample was taken and characterized by $^1$H NMR spectroscopy. It was determined that about 50% of the material was hydrochlorinated. Dissolution into hexanes and bubbling dry HCl for an additional 6 hours at 0° C. did not improve the yield. 1-methyldichlorosilyl-3-methyl-3-chlorobutane was finally separated from the olefins by recrystallization at −80° C. and −22° C. First, the mixture obtained after hydrochlorination was dissolved in 50 ml of hexanes and cooled to −80° C. White crystals precipitated which were isolated by pouring the hexanes solution out of the flask. The flask was allowed to warm to room temperature and was transferred to the freezer at −22° C. A crystalline material separated from the liquid phase at −22° C. The liquid phase was transferred to another flask in a closed system while it was still at −22° C. and the crystals were held under vacuum for 3 hours to evaporate solvents. The isolated crystals were confirmed by $^1$H NMR to be the target product 1-methyldichlorosilyl-3-methyl-3-chlorobutane (INITIATOR 2)

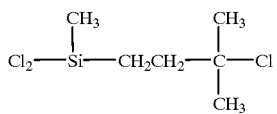

The above experiments illustrate the difficulty of preparing this compound.

(Comparative) Example 6
Polymerization of isobutylene Using the Functional Initiator 1-methyldichlorosilyl-3-methyl-3-chloro-butane INITIATOR 2, prepared above, was used to polymerize IB under identical conditions to those used in Example 3. The polymerization was quite rapid and resulted in PIB having very high number average molecular weight (20,000 to about 100,000). Due to the high molecular weights, structural information on the head groups could not be obtained. Final molar concentrations of the reactants (based on the total solution) were as follows:
INITIATOR 2=$2 \times 10^{-2}$M; DTBP=$3 \times 10^{-3}$M; TiCl$_4$=$8 \times 10^{-2}$M; IB=1.0M.

The molecular weights obtained using INITIATOR 2 were much higher than calculated values, an indication that a significant portion of this compound did not act as an initiator in the above attempted polymerization. From a practical perspective, such inability to control molecular weight makes this initiator unsuited for commercial applications.

That which is claimed is:
1. A compound having the formula

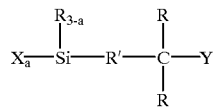

wherein R is independently selected from the group consisting of alkyl groups having 1 to 10 carbon atoms and aryl groups having 6 to 10 carbon atoms, R' is a divalent aliphatic hydrocarbon group having at least 3 carbon atoms, X is halogen, Y is selected from the group consisting of halogen, alkoxy, acyloxy and hydroxyl groups and a is 2 or 3.

2. The compound according to claim 1, wherein R' has 3 to 10 carbon atoms.

3. The compound according to claim 1, wherein R is methyl.

4. The compound according to claim 3, wherein X and Y are chlorine.

5. The compound according to claim 4, having the structure

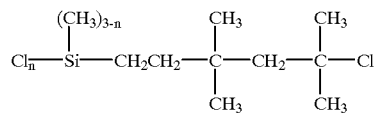

in which n is 2 or 3.

* * * * *